(12) United States Patent
Wolf et al.

(10) Patent No.: US 10,286,013 B2
(45) Date of Patent: May 14, 2019

(54) PANCREATIC ISLETS OF TRANSGENIC LEA29Y ANIMALS FOR TREATING DIABETES

(71) Applicant: MWM Biomodels GmbH, Tiefenbach (DE)

(72) Inventors: Eckhard Wolf, Vierkirchen (DE); Nikolai Klymiuk, Hohenkammer (DE); Lelia Wolf-Van Buerck, Aschheim (DE); Jochen Seißler, München (DE)

(73) Assignee: MWM BIOMODELS GMBH, Tiefenbach (DE)

( * ) Notice: Subject to any disclaimer, the term of this patent is extended or adjusted under 35 U.S.C. 154(b) by 0 days.

(21) Appl. No.: 15/336,350

(22) Filed: Oct. 27, 2016

(65) Prior Publication Data

US 2017/0042942 A1 Feb. 16, 2017

Related U.S. Application Data

(63) Continuation of application No. 13/659,523, filed on Oct. 24, 2012, now abandoned.

(51) Int. Cl.
| | | |
|---|---|---|
| A61K 35/39 | (2015.01) | |
| A01K 67/027 | (2006.01) | |
| A61K 35/54 | (2015.01) | |
| C12N 15/85 | (2006.01) | |
| C07K 14/705 | (2006.01) | |

(52) U.S. Cl.
CPC .......... A61K 35/39 (2013.01); A01K 67/0275 (2013.01); A61K 35/54 (2013.01); C07K 14/70521 (2013.01); C12N 15/85 (2013.01); C12N 15/8509 (2013.01); A01K 2207/15 (2013.01); A01K 2217/00 (2013.01); A01K 2217/052 (2013.01); A01K 2227/105 (2013.01); A01K 2227/108 (2013.01); A01K 2267/025 (2013.01); C07K 2319/00 (2013.01)

(58) Field of Classification Search
None
See application file for complete search history.

(56) References Cited

U.S. PATENT DOCUMENTS

| | | | |
|---|---|---|---|
| 7,919,673 | B2 | 4/2011 | Wolf et al. |
| 2003/0022836 | A1 | 1/2003 | Larsen et al. |
| 2003/0157705 | A1 | 8/2003 | Fodor et al. |
| 2011/0038841 | A1* | 2/2011 | Ayares ............... A01K 67/0276 424/93.21 |

FOREIGN PATENT DOCUMENTS

| | | |
|---|---|---|
| EP | 0877555 | 8/2007 |
| EP | 1397153 | 4/2008 |
| EP | 1924686 | 5/2008 |
| EP | 2077330 | 7/2009 |
| WO | WO 1993-00431 | 1/1993 |
| WO | WO 1997-11607 | 4/1997 |
| WO | WO 2001-92337 | 12/2001 |
| WO | WO 2007-035213 | 3/2007 |

OTHER PUBLICATIONS

Bahr, A. et al., "Establishment of LEA29Y Transgenic Donor Pigs for Xenotransplantation," Jul. 17-19, 2011, Abstract only, p. 1, *Swine in Biomedical Research Conference*, Chicago, IL.

Bahr, A., "(Re)producing transgenic pigs for xenotransplantation—selection of founder animals and establishment of breeding herds. Ph.D. Dissertation." University of Munich, Germany, published on-line Oct. 15, 2011. p. 1-177.

Cardona K. et al., "Long-term survival of neonatal porcine islets in nonhuman primates by targeting costimulation pathways," *Nature Medicine*, Mar. 2006, vol. 12, No. 3, p. 304-306.

Elliot et al., "Live encapsulated porcine islets from a type 1 diabetic patient 9.5 yr after xenotransplantation." *Xenotransplantation*, Mar. 2007, 14(2): 157-161.

Hering BJ. et al., "Prolonged diabetes reversal after intraportal xenotransplantation of wild-type porcine islets in immunosuppressed nonhuman primates," *Nature Medicine*, Mar. 2006, vol. 12, No. 3, p. 301-303.

Issa F. et al., "The where and when of T cell regulation in transplantation," *Trends in Immunology*, Mar. 2013, vol. 34, No. 3, p. 107-113.

Kawai T. et al., "Thromboembolic complications after treatment with monoclonal antibody against CD40 ligand," *Nature Medicine*, Feb. 2000, vol. 6, No. 2, p. 114.

Kebler, B. et al., "New pigs for xenotransplantation, part 2—strategies to overcome cellular rejection," Jun. 3-4, 2010, Abstract only, p. 1, 13$^{th}$ *Minisymposium Xenotransplantation of the German Working Group*, Berlin.

Klymiuk, N. et al., "High-level expression of LEA29Y in pancreatic islets of transgenic pigs," Jan. 9-13, 2010, Abstract only, p. 1, 36$^{th}$ *Annual Conference of the IETS/23$^{rd}$ Annual Meeting SBTE*, Cordoba, Argentina.

Klymiuk, N. et al., "Xenografted Islet Cell Clusters From INSLEA29Y Transgenic Pigs Rescue Diabetes and Prevent Immune Rejection in Humanized Mice," *Diabetes*, Jun. 2012, pp. 1527-1532, vol. 61.

Martin C. et al., "Transgenic expression of CTLA4-Ig by fetal pig neurons for xenotransplantation," *Transgenic Research*, Aug. 2005, vol. 14, No. 4, p. 373-384.

Mirenda, V. et al., "Achieving Permanent Survival of Islet Xenografts by Independent Manipulation of Direct and Indirect T-Cell Responses," *Diabetes*, Apr. 2005, pp. 1048-1055, vol. 54.

O'Connell PJ. et al., "Transplantation of Xenogeneic Islets: Are We There Yet?" *Current Diabetes Reports*, Aug. 2013, vol. 13, p. 687-694.

(Continued)

Primary Examiner — Scott Long
Assistant Examiner — Arthur S Leonard
(74) Attorney, Agent, or Firm — Saliwanchik, Lloyd & Eisenschenk

(57) ABSTRACT

The present invention relates to methods of treating diabetes in a human subject comprising the use of pancreatic islets or of embryonic pancreatic tissue of a transgenic animal, wherein said transgenic animal contains a polynucleotide sequence encoding a CTLA4 peptide-immunoglobulin fusion, preferably LEA29Y, and expresses said CTLA4 peptide-immunoglobulin fusion in a tissue-specific manner in pancreatic islets.

16 Claims, 7 Drawing Sheets

Specification includes a Sequence Listing.

(56) References Cited

OTHER PUBLICATIONS

Sykes M. et al., "Clinical trial of islet xenotransplantation in Mexico," *Xenotransplantation*, Sep. 2006, vol. 13, No. 5, p. 371-372.
Valdes-Gonzalez et al., "Xenotransplantation of porcine neonatal islets of Langerhans and Sertoli cells: a 4-year study." *European Journal of Endocrinology*, 2005, 153: 419-427.
Van Buerck, L. et al., "Islet grafts from neonatal *INS*-LEA29Y transgenic pigs reverse diabetes in streptozotocin-treated NSG mice," Jun. 1-4, 2011, Abstract only, p. 1, *IPITA Congress*, Prague.
Van Buerck, L. et al., "Local LEA29Y expression prevents xenogeneic rejection of porcine neonatal islet-like clusters in humanized mice," Jan. 29-31, 2012, Abstract only, p. 1, $2^{nd}$ *Joint AIDPIT and EPITA Winter Symposium*, Igis, Austria.
Van Buerck, L. et al., "Lokale LEA29Y Expression verhindert die Abstobung porziner Inselzellcluster im humanisierten Mausmodell," Mai 16-19, 2012, Abstract only, p. 1, *Jahrestagung Deutsche Diabetesgesellschaft*, Stuttgart.
Van Buerck, L. et al., "Transplantation of neonatal islets from LEA29Y-transgenic pigs restores normoglycemia in streptozotocin-diabetic NSG-mice," Jan. 23-25, 2011, Abstract only, p. 1, $30^{th}$ *AIDPIT Workshop*, Igls, Austria.
Van Der Windt DJ. et al., Clinical islet xenotransplantation: how close are we? *Diabetes*, Dec. 2012, vol. 61, No. 12, p. 3046-3055.
Van Der Windt DJ. et al., "Long-term controlled normoglycemia in diabetic non-human primates after transplantation with hCD46 transgenic porcine islets," *American Journal of Transplantation*, Dec. 2009, vol. 9, No. 12, p. 2716-2726.
Yang YG. et al., "Xenotransplantation: current status and a perspective on the future," *Nature Reviews: Immunology*, Jul. 2007, vol. 7, No. 7, p. 519-531.

\* cited by examiner

SEQUENCE LISTING

```
<160> NUMBER OF SEQ ID NOS: 1

<210> SEQ ID NO 1
<211> LENGTH: 383
<212> TYPE: PRT
<213> ORGANISM: Artificial
<220> FEATURE:
<223> OTHER INFORMATION: LEA29Y fusion protein

<400> SEQUENCE: 1

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
                20                  25                  30

Ala Val Val Leu Ala Ser Ser Arg Gly Ile Ala Ser Phe Val Cys Glu
            35                  40                  45

Tyr Ala Ser Pro Gly Lys Tyr Thr Glu Val Arg Val Thr Val Leu Arg
        50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
                100                 105                 110

Thr Gly Leu Tyr Ile Cys Lys Val Glu Leu Met Tyr Pro Pro Pro Tyr
            115                 120                 125

Tyr Glu Gly Ile Gly Asn Gly Thr Gln Ile Tyr Val Ile Asp Pro Glu
        130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270
```

```
Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
        290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
                340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
        370                 375                 380
```

PANCREATIC ISLETS OF TRANSGENIC LEA29Y ANIMALS FOR TREATING DIABETES

CROSS-REFERENCE TO A RELATED APPLICATION

This application is a Continuation application of co-pending application U.S. Ser. No. 13/659,523, filed Oct. 24, 2012, which is incorporated herein by reference in its entirety.

The Sequence Listing for this application is labeled "SeqList_24Jan13_ST25.txt", which was created on Jan. 24, 2013, and is 4 KB. The entire content is incorporated herein by reference in its entirety.

FIELD OF THE INVENTION

The present invention relates to methods of treating diabetes in a human subject comprising the use of pancreatic islets or of embryonic pancreatic tissue of a transgenic animal, wherein said transgenic animal contains a CTLA4 peptide-immunoglobulin fusion, preferably LEA29Y, and expresses said CTLA4 peptide-immunoglobulin fusion in a tissue-specific manner in pancreatic islets.

BACKGROUND OF THE INVENTION

Type 1 diabetes is a chronic metabolic disease associated with development of severe complications (Nathan et al., 2009). It has been shown that type 1 diabetes can be cured by the transplantation of the pancreas or isolated islets of Langerhans. Nonetheless, the success of pancreas and islet transplantation is limited by the shortage of organ donors and the need for systemic immunosuppressive therapy (Robertson, 2010) and is therefore restricted to few patients (CITR, 2007).

If enough donor islets were available, type 2 diabetics also would profit from islet transplantation, if insulin supplementation is required, when other treatments are insufficient, or if they suffer from specific β-cell defects (Bottino & Trucco, 2005).

Limited availability of human donor organs may be overcome by the use of animals, in particular pigs, as organ donors. Pig-to-human xenotransplantation faces the problem of strong rejection predominantly by direct T cell recognition of pig major histocompatibility complex (MHC) and indirect T cell response to xenogeneic antigens presented by the recipient antigen-presenting cells (APCs) (Clarkson & Sayegh, 2005).

Recent advances in immunosuppressive therapies provided evidence that transplanted porcine islets can promote long-lasting cure of diabetes in nonhuman primates (Cardona et al., 2006, Hering et al., 2005, Cardona et al., 2007). However, the currently used intensive immunosuppressive regimen in pig islet transplantation may have severe side effects in humans and cannot be transferred into clinical practice. Blockade of the B7/CD28 co-stimulatory pathway by LEA29Y, a high affinity variant of the CTLA-4Ig fusion protein (Larsen et al., 2005), has been shown to be effective in clinical trials following kidney transplantation (Durrbach et al., 2010, Vincenti et al., 2010) and in porcine islet transplantation studies (Cardona et al., 2006 and 2007; Tchorch-Yutsis, 2009).

Phelps et al. (2009) disclose the production and characterization of transgenic pigs expressing porcine CTLA4-Ig. However, the transgenic pigs exhibited robust and ubiquitous expression of pCTLA4-Ig and the expression of pCTLA4-Ig resulted in acute susceptibility to opportunistic pathogens due at least in part to a significantly compromised humoral immune status. The authors found that, as CTLA4-Ig molecule is known to have immunosuppressive activity, high levels of pCTLA4-Ig expression in the blood, as well as defective development related to exposure to pCTLA4-Ig in utero, contributed to the reduced immune status. Therefore, prophylactic treatment with antibiotics appears to be necessary to promote survival of disease-free transgenic pigs to a size optimal for organ procurement for transplantation.

US 2009/0186097 A1 discloses the use of two vector constructs containing CTLA4-Ig, driven by the two different promoters, for transfecting fetal fibroblast cell lines. According to Example 5 of US 2009/0186097, cell populations and cloned colonies that screen positive for the presence of a CTLA4-Ig construct can be used as nuclear donors to produce CTLA4-Ig transgenic pigs by nuclear transfer. However, no transgenic pigs are described in the application. Only one kind of transgenic pigs which were generated using a plasmid construct for CTLA4-Ig driven by the chicken beta-actin promoter has later been published and turned out to be not a realistic option for xenotransplantation, see Phelps et al., 2009 as discussed above.

Thus, there is a need in the art for improved means and methods of treating diabetes in patients, in particular for providing suitable donor animals.

SUMMARY OF THE INVENTION

According to the present invention this object is solved by a method of treating diabetes in a human subject, comprising the steps of isolating pancreatic islets of a transgenic animal and administering said isolated pancreatic islets of the transgenic animal into a human subject in need thereof, wherein said transgenic animal is a transgenic animal whose genome comprises a recombinant nucleic acid comprising a polynucleotide sequence encoding a CTLA4 peptide fused to an immunoglobulin ("CTLA4 peptide-immunoglobulin fusion") wherein said polynucleotide sequence is operably linked to an insulin promoter that results in expression of the CTLA4 peptide-immunoglobulin fusion, wherein said animal expresses the CTLA4 peptide-immunoglobulin fusion, and wherein said animal exhibits, as a result of the expression of said CTLA4 peptide-immunoglobulin fusion, tissue-specific expression of the CTLA4 peptide-immunoglobulin fusion in pancreatic islets.

According to the present invention this object is solved by a method of treating diabetes in a human subject, comprising the steps of isolating transgenic embryonic pancreas or transgenic embryonic pancreatic tissue of a transgenic animal and administering said isolated embryonic pancreas or said isolated embryonic pancreatic tissue of the transgenic animal into a human subject in need thereof, wherein said transgenic animal is a transgenic animal whose genome comprises a recombinant nucleic acid comprising a polynucleotide sequence encoding a CTLA4 peptide fused to an immunoglobulin ("CTLA4 peptide-immunoglobulin fusion") wherein said polynucleotide sequence is operably linked to an insulin promoter that results in expression of the CTLA4 peptide-immunoglobulin fusion, wherein said animal expresses the CTLA4 peptide-immunoglobulin fusion, and wherein said animal exhibits, as a result of the CTLA4 peptide-immunoglobulin fusion in the transgenic embryonic pancreas or transgenic embryonic pancreatic tissue. Said tissue-specific expression of the CTLA4 peptide-immunoglobulin fusion also occurs in the pancreatic islets of the xenogeneic tissue administered to the recipient.

DESCRIPTION OF THE PREFERRED EMBODIMENTS OF THE INVENTION

Figure 1A:
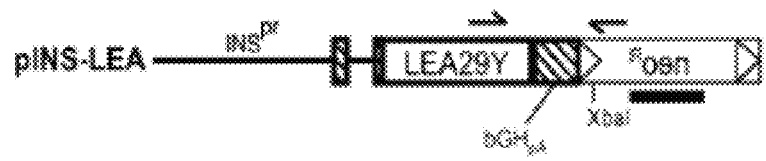
FIGS. 1A-1C—Generation of INSLEA29Y Transgenic (LEA-Tg) Pigs.
(A) The vector consisted of the 1.3 kb regulatory sequence from the porcine INS gene, the LEA29Y coding sequence, and the poly-adenylation box from the bovine GH gene. Regulatory sequences are depicted as lines whereas exonic structures are boxed. Untranslated regions are shaded. The selection cassette provides resistance to neomycin. Binding sites for primers are indicated as arrows and the probe for Southern blot hybridization is shown as a bold line. (B) Southern blotting of 7 founders was performed on XbaI digested genomic DNA with a probe binding to the neomycin resistance cassette. (C) Immunohistochemical staining for LEA29Y on tissue sections from a neonatal transgenic pig (age 2 days, pancreas, C2), an adult founder animal (age 3 months; pancreas, liver, lung, kidney, and spleen, C4, 5-8), and from age-matched wild-type control pigs (pancreas, C1, 3). Scale bar: 100 µm.

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Method of Treating Diabetes by Using Transgenic Pancreatic Islets

As described above, the present invention provides a method of treating diabetes in a human subject.
Said method comprises the steps of
    isolating transgenic pancreatic islets of a transgenic animal, and
    administering said isolated transgenic pancreatic islets of the transgenic animal into a human subject in need thereof.

Preferably, the diabetes treated according to the method of the invention is diabetes type 1 and/or diabetes type 2.

Transgenic Animals

The transgenic animal used (as donor animal of the pancreatic islets) in the method of the invention is a transgenic animal whose genome comprises a recombinant nucleic acid comprising a polynucleotide sequence encoding CTLA4 peptide fused to an immunoglobulin ("CTLA4 peptide-immunoglobulin fusion") wherein the polynucleotide sequence is operably linked to an insulin promoter that results in expression of the CTLA4 peptide-immunoglobulin fusion.

A "nucleic acid" according to the invention refers to polynucleotides, such as DNA, RNA, modified DNA, modified RNA as well as mixtures thereof.

Preferably, the transgenic animal is a pig, bovine, or small ruminant, such as sheep or goat.

More preferably, the transgenic animal is a pig.

The transgenic animal expresses the CTLA4 peptide-immunoglobulin fusion. The transgenic animal exhibits, as a result of the expression of said CTLA4 peptide-immunoglobulin fusion, tissue-specific expression of the CTLA4 peptide-immunoglobulin fusion in pancreatic islets.

Preferably, the transgenic animal does not exhibit an immunodeficient phenotype. In particular, sterile breeding conditions are not required for the expansion of the breeding colony. Preferably, sterile breeding conditions, in particular designated pathogen-free (DPF) breeding conditions (as described in Schuurman 2009), are required before isolation of the pancreatic islets for xenotransplantation.

The polynucleotide sequence encodes a CTLA4 peptide fused to an immunoglobulin ("CTLA4 peptide-immunoglobulin fusion").

CTLA-4 (Cytotoxic T-Lymphocyte Antigen 4), also known as CD152, is a protein receptor that down-regulates the immune system. CTLA4 is a molecule crucial for T-cell co-stimulation, selectively blocking the process of T-cell activation.

CTLA4 is a member of the immunoglobulin superfamily, which is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

A "CTLA4 peptide" as used herein can be full length CTLA4, or a biologically active fragment or derivative thereof. Typically, the fragment would be at least 50%, 60%, 70%, 80%, 90%, or 95% of the full length CTLA4. In one embodiment, the CTLA4 peptide is human or porcine CTLA4. The CTLA4 peptide can be truncated, such as by removing at least the transmembrane domain of CTLA4. The CTLA peptide can be the extracellular domain of CTLA4 or biologically active fragment thereof wherein the fragment would typically be at least 50%, 60%, 70%, 80%, 90%, or 95% of the full length extracellular domain. The CTLA4 peptide can be mutated.

Preferably, a CTLA4 peptide is a human CTLA4 peptide mutated by substitution of an alanine at position +29 with a tryptophan, and a leucine at position +104 with a glutamic acid (LEA29Y). The CTLA4 peptide can be modified, such as by addition of an intracellular retention signal.

The CTLA4 peptide is fused to an immunoglobulin (Ig), or a biologically active fragment or derivative thereof. The immunoglobulin can be IgG, such as IgG1 or IgG4.

A fusion protein CTLA4-Ig is commercially available as Orencia (Abatacept). A second generation form of CTLA4-Ig is known as Belatacept.

LEA29Y (Belatacept) is a fusion protein composed of the Fc fragment of a human IgG1 immunoglobulin linked to the extracellular domain of CTLA-4 (Larsen et al., 2005). Belatacept was developed by Bristol-Myers-Squibb.

In a preferred embodiment, the recombinant nucleic acid encodes the CTLA4 peptide-immunoglobulin fusion that is LEA29Y.

Preferably, the recombinant nucleic acid encodes a protein comprising or having the sequence of SEQ ID NO: 1.

Preferably, the recombinant nucleic acid encodes a protein comprising or having an amino acid sequence with at least 90%, at least 95% or at least about 99% sequence identity to the sequence of SEQ ID NO: 1, wherein the alanine at position +29 is substituted with a tryptophan, and the leucine at position +104 is substituted with a glutamic acid.

SEQ ID NO: 1 shows the amino acid sequence of LEA29Y.

Preferably, the polynucleotide sequence encoding the CTLA4 peptide-immunoglobulin fusion, preferably LEA29Y, is part of an expression construct or expression vector.

Any method for introducing the expression construct or vector into early embryos can be utilized. Preferably, the expression constructs or vectors can be introduced into somatic cells or stem cells, which will then be used for nuclear transfer to generate cloned transgenic animals.

In one embodiment, the polynucleotide sequence encoding the CTLA4 peptide-immunoglobulin fusion, preferably LEA29Y, is incorporated into a plasmid or viral vector.

The expression construct or expression vector, plasmid or viral vector comprises a promoter that allows for expressing the CTLA4 peptide-immunoglobulin fusion, preferably LEA29Y, in the transgenic pig, preferably allows expression in the pancreatic islets, and preferably the β-cells of the pancreas.

A preferred promoter is an insulin promoter, more preferably pig INS promoter. Further suitable promoters are the rat insulin 2 gene promoter (RIPII) or other promoters that confer expression in the pancreatic islets, such as PDX1.

Preferably, the recombinant nucleic acid is an expression construct comprising pig INS promoter.

A preferred expression construct is shown in FIG. 1a.

Preferably, the transgenic animal contains the recombinant nucleic acid in its germ cells and somatic cells.

In one embodiment, LEA29Y is expressed in the pancreatic islets of the transgenic animal, including the β-cells.

Isolation and Administration

According to a method of the invention, the transgenic pancreatic islets of the transgenic animal are isolated according to state of the art methods (reviewed in Toso et al., 2000, Ulrichs et al., 2012 and London et al., 1998).

In one embodiment, the isolated transgenic pancreatic islets are administered to the human subject by xenotransplantation.

As used herein, the term "xenotransplantation" refers to the administration of living cells, tissues or organs from one species to another. Such cells, tissues or organs are called "xenografts" or "xenotransplants". As used herein, the term "xenotransplantation" preferably refers to the administration of animal living cells, tissues or organs to a subject, i.e. a human recipient.

According to the invention, after xenotransplantation of said transgenic pancreatic islets of said animal into a human subject or into humanized animal models, said transgenic pancreatic islets are protected from rejection by the host immune system.

Preferably, the patient requires less administration of immunosuppressive agents compared to standard therapy and/or compared to (xeno)transplantation of wild type pancreatic islets of an animal.

Preferably, the transgenic pancreatic islets—after (xeno)transplantation into the recipient—display the same potential to normalize glucose homeostasis as wild type cells.

In one embodiment, the isolated transgenic pancreatic islets are encapsulated or micro-encapsulated before administration.

The isolated transgenic pancreatic islets can be encapsulated or micro-encapsulated before administration with a gel or (immunologically inert) polycarbohydrate(s) or polysaccharide(s), such as alginate or alginate comprising further components, such as alginate-polyornithine-alginate.

Preferably, the encapsulated or micro-encapsulated transgenic pancreatic islets are administered by implantation, preferably into a patient's abdomen using a laparoscopic procedure.

For example, the transgenic pancreatic islets can be encapsulated or micro-encapsulated and then transplanted as described before (see, for example, Elliot et al. 2005 and Elliot et al. 2007).

Method of Treating Diabetes by Using Transgenic Embryonic Pancreatic Tissue or Embryonic Pancreas As described above, the present invention provides a further method of treating diabetes in a human subject.
Said method comprises the steps of:
isolating embryonic pancreas or embryonic pancreatic tissue of a transgenic animal, and
administering said isolated embryonic pancreas or said isolated embryonic pancreatic tissue of the transgenic animal into a human subject in need thereof.

Preferably, the diabetes treated according to the method of the invention is diabetes type 1 and/or diabetes type 2.

The term "embryonic pancreas" and "embryonic pancreatic tissue" as used herein refers to pancreas or parts of pancreas isolated from pig foetuses between about 30 and 60 days after conception, preferably between about 36 and 48 days after conception, more preferably between 39 and 45 days after conception, and even more preferably about 42 days after conception (pig specific) or functionally equivalent stages in other species.

The transgenic animal used (as donor animal of the embryonic pancreas or embryonic pancreatic tissue) in the method of the invention is a transgenic animal whose genome comprises a recombinant nucleic acid comprising a polynucleotide sequence that encodes a CTLA4 peptide fused to an immunoglobulin ("CTLA4 peptide-immunoglobulin fusion") wherein the polynucleotide sequence is operably linked to an insulin promoter that results in expression of the CTLA4 peptide-immunoglobulin fusion, i.e. is a transgenic animal as described herein above.

A "nucleic acid" according to the invention refers to polynucleotides, such as DNA, RNA, modified DNA, modified RNA as well as mixtures thereof.

Preferably, the transgenic animal is a pig, bovine, or small ruminant, such as sheep or goat.

More preferably, the transgenic animal is a pig.

The transgenic animal expresses the CTLA4 peptide-immunoglobulin fusion. The transgenic animal exhibits, as a result of the expression of said CTLA4 peptide-immunoglobulin fusion, tissue-specific expression of the CTLA4 peptide-immunoglobulin fusion in the embryonic pancreas or embryonic pancreatic tissue.

Preferably, tissue-specific expression of the CTLA4 peptide-immunoglobulin fusion also occurs in the pancreatic islets of the xenogeneic tissue (i.e. the embryonic pancreas or embryonic pancreatic tissue) administered to the subject.

Preferably, the transgenic animal does not exhibit an immunodeficient phenotype. In particular, sterile breeding conditions are not required for the expansion of the breeding colony. Preferably, sterile breeding conditions, in particular designated pathogen-free (DPF) breeding conditions (as described in Schuurman 2009), are required before isolation of the embryonic pancreas or embryonic pancreatic tissue for xenotransplantation.

The polynucleotide sequence encodes a CTLA4 peptide fused to an immunoglobulin ("CTLA4 peptide-immunoglobulin fusion"), as described herein.

Preferably, the transgenic animal contains the recombinant nucleic acid in its germ cells and somatic cells.

In one embodiment, the CTLA4 peptide-immunoglobulin fusion, preferably LEA29Y, is expressed in the embryonic pancreas or embryonic pancreatic tissue and in the pancreatic islets of the xenogeneic tissue administered to the subject.

Preferably, the transgenic pancreatic islets of said animal display the same potential to normalize glucose homeostasis as wild type cells.

Isolation and Administration

According to a method of the invention, the embryonic pancreas or embryonic pancreatic tissue of the transgenic animal is isolated.

Thereby, the embryonic pancreas and/or embryonic pancreatic tissue is/are isolated from pig foetuses isolated between about 30 and 60 days after conception, preferably between about 36 and 48 days after conception, more preferably between 39 and 45 days after conception, and even more preferably about 42 days after conception (pig specific) or functionally equivalent stages in other species, as described by Hecht et al., 2009.

In one embodiment, the isolated transgenic embryonic pancreas or embryonic pancreatic tissue is administered to the human subject by xenotransplantation, such as by implantation into the omentum or other sites allowing survival of the xenograft and functional insulin secretion.

Methods of transplantation and/or implantation are described in Hecht et al., 2009.

Preferably, the transgenic embryonic pancreas or embryonic pancreatic tissue grows at the transplantation site of the recipient.

According to the invention, after xenotransplantation/implantation of said transgenic embryonic pancreas or embryonic pancreatic tissue of said animal into a human subject or into a humanized animal model, said transgenic embryonic pancreas or embryonic pancreatic tissue is protected from rejection by the host immune system.

Preferably, the subject requires less administration of immunosuppressive agents compared to standard therapy and/or compared to (xeno)transplantation of wild type pancreatic islets of an animal.

Preferred Embodiments of the Invention

Local expression of LEA29Y restricted to the transplantation site represents an innovative approach to protect grafted islets from xenogeneic immune rejection without the side effects of systemic immunosuppression. Therefore, the inventors generated transgenic pigs expressing LEA29Y specifically in pancreatic β-cells and demonstrate for the first time the potential of neonatal INSLEA29Y transgenic (LEA-tg) islet clusters to normalize blood glucose levels and evaluate the inhibition of human-anti-pig rejection in a humanized NOD-scid IL2Rgamma$^{null}$ (NSG) model.

Islet transplantation is a potential treatment for diabetes, in particular for type 1 diabetes, but the shortage of donor organs limits its routine application. As donor animals the inventors generated transgenic pigs expressing LEA29Y, a high-affinity variant of the T cell co-stimulation inhibitor CTLA-4Ig, under the control of the porcine insulin promoter. Neonatal islet-cell-clusters (ICCs) from INSLEA29Y transgenic (LEA-tg) pigs and wild-type controls were transplanted into streptozotocin-induced hyperglycemic NOD-scid IL2Rgamma$^{null}$ (NSG) mice. Cloned LEA-tg pigs are healthy and exhibit a strong β-cell-specific transgene expression. LEA-tg ICCs displayed the same potential to normalize glucose homeostasis as wild-type ICCs after transplantation. After adoptive transfer of human peripheral blood mononuclear cells (PBMCs), transplanted LEA-tg ICCs were completely protected from rejection, whereas re-occurrence of hyperglycemia was observed in 80% of mice transplanted with wild-type ICCs. Herewith, the inventors provide the first proof-of-principle report on transgenic pigs with β-cell-specific expression of a LEA29Y and their successful application as donors in a xenotransplantation model.

If enough donor islets were available, type 2 diabetics also can profit from islet transplantation, if insulin supplementation is required, when other treatments are insufficient, or if they suffer from specific β-cell defects (Bottino & Trucco, 2005).

Results

Generation of INSLEA29Y Transgenic (LEA-Tg) Pigs

Figure 1B:
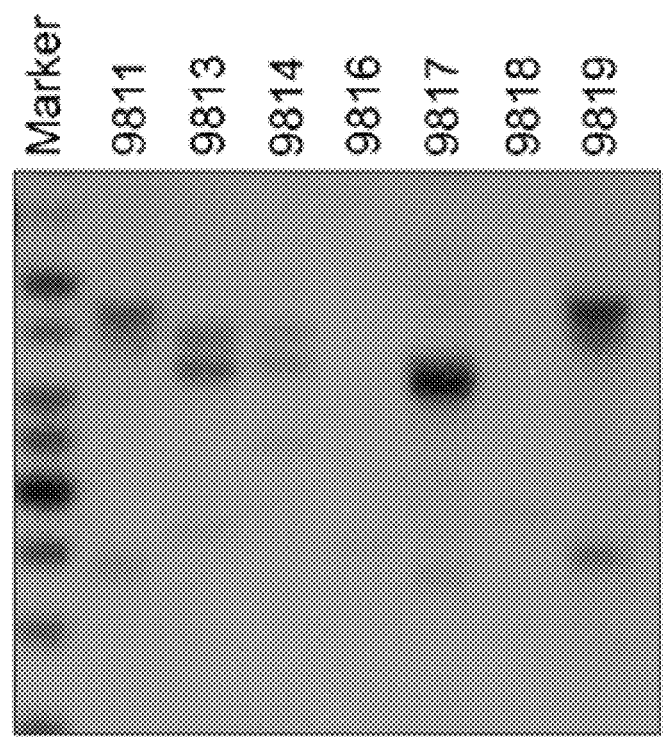
Figure 1C:
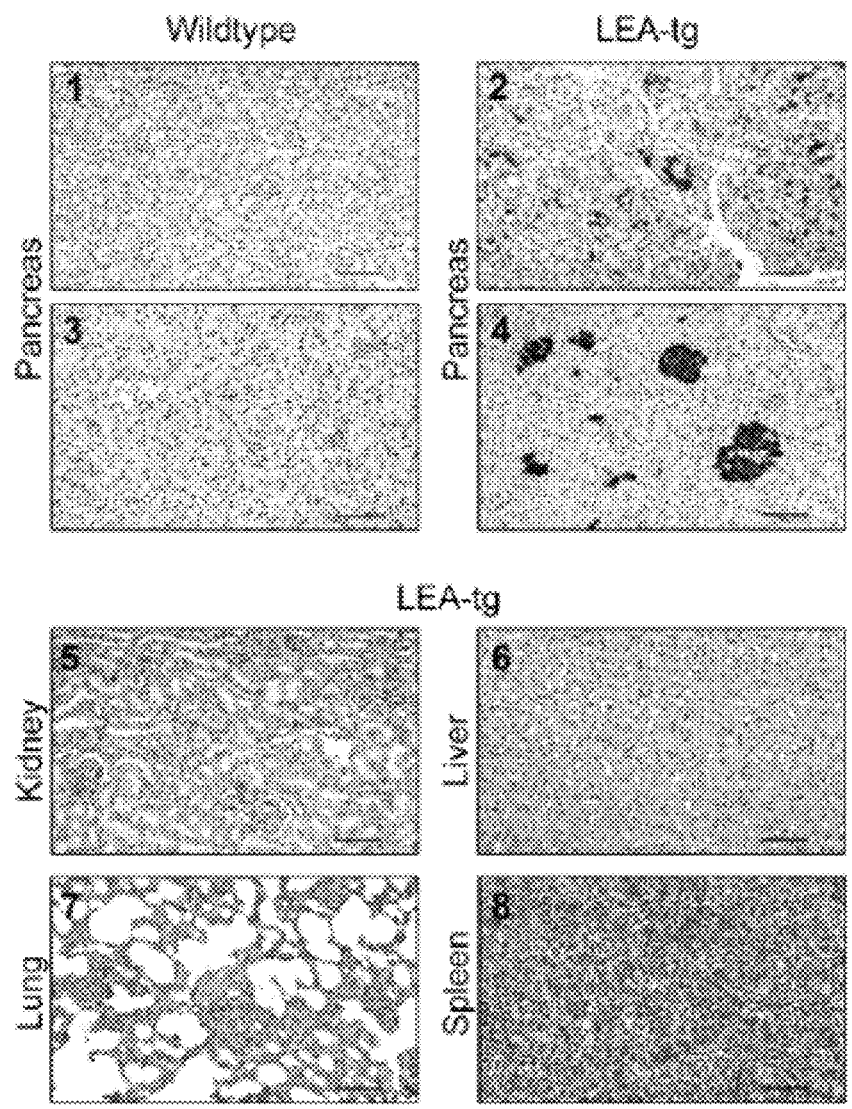

The INSLEA29Y expression construct (FIG. 1A) was used for nucleofection of porcine fetal fibroblasts, and stable cell clones were pooled and used for nuclear transfer (Aigner et al., 2010). Cloned embryos (n=216) were transferred to three synchronized gilts, resulting in two pregnancies with nine born piglets including two stillborns. Seven of eight genotyped piglets were transgenic, each representing a unique founder, as demonstrated by Southern blot analysis (FIG. 1B). Four of these animals were sacrificed at the age of three months for immunohistochemical staining of different organs (FIG. 1C). Transgenic pigs displayed a strong LEA29Y staining in the pancreatic islets (FIG. 1C). Re-cloned animals served as islet donors or were raised for future breeding purposes. These pigs are fertile, have no signs of opportunistic infections, and exhibit normal blood glucose levels.

Differentiation and Maturation of Transplanted Islet-Cell-Clusters

Figure 2A:
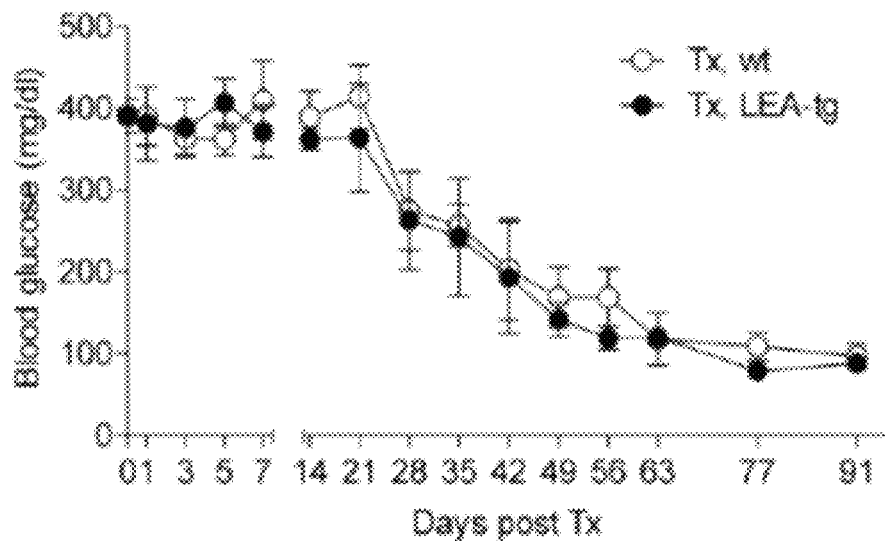
FIGS. 2A-2D—Grafted LEA-Tg ICCs Display Physiological β-Cell Function.
Course of blood glucose levels after transplantation (A), i.p. glucose tolerance testing (performed 10 days after the development of normoglycemia, (B), and immunohistochemistry of grafted ICCs (7-9 days after transplantation (C) and 4.0-4.5 months after transplantation (normoglycemic animals, (D) in mice transplanted with wild-type (Tx, wt) and in mice transplanted with LEA-tg (Tx, LEA-tg) ICCs. Mice of both transplantation groups developed stable normoglycemia (A) and restored glucose tolerance ((B), bottom), by porcine insulin secretion ((B), top). The area under the curve (AUC) for glucose and insulin (B) during i.p.GTT was comparable in both transplantation groups. Immunohistochemical staining of serial sections from the transplantation site against insulin and IgG revealed insulin/LEA29Y expression in a minor proportion of ICCs a few days after transplantation (C). In contrast, after the development of normoglycemia the transplanted cells have differentiated into a widespread insulin positive stained tissue in both transplantation groups with LEA29Y transgene expression restricted to the grafted ICCs from transgenic pigs (D). Scale bar: 100 µm. n=5 for each transplantation group.
Figure 2B:
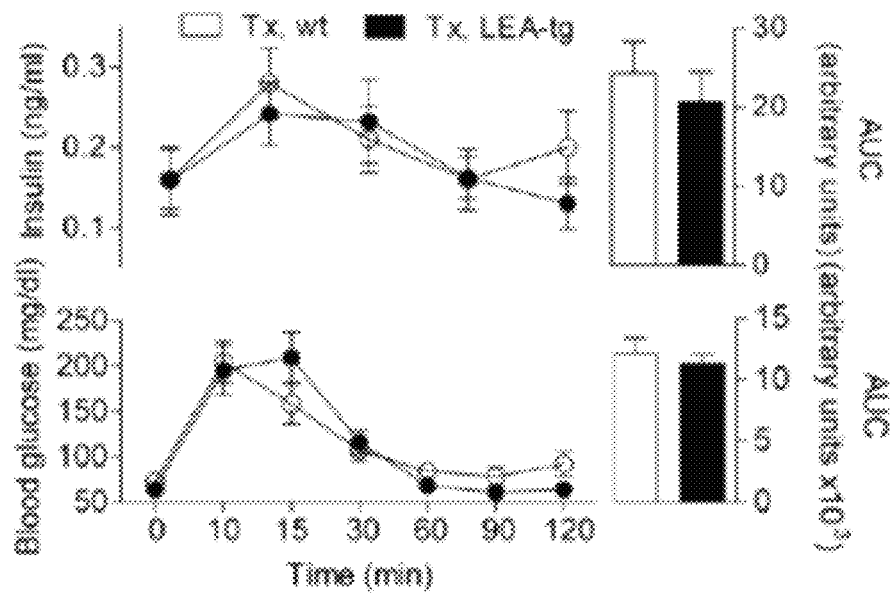
Figure 2C:
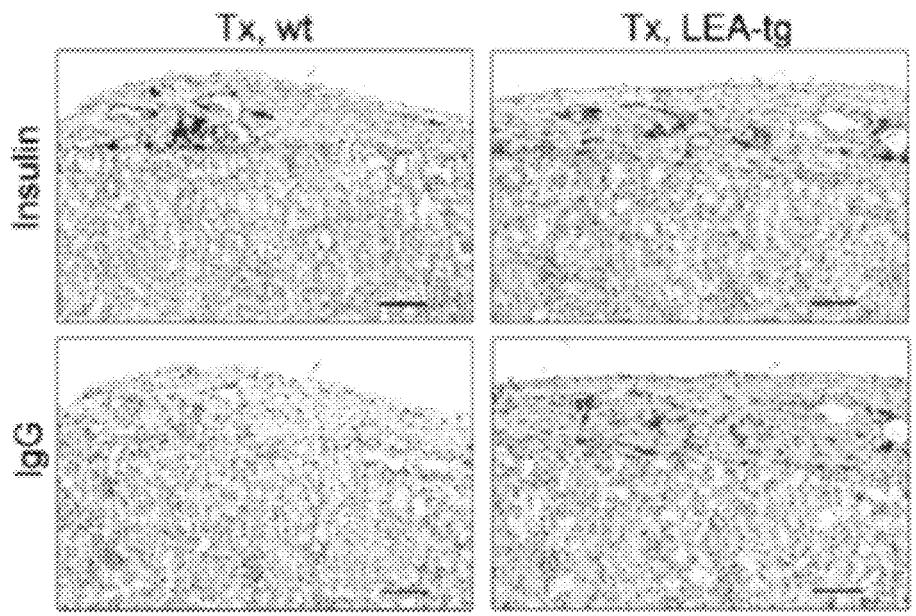
Figure 2D:
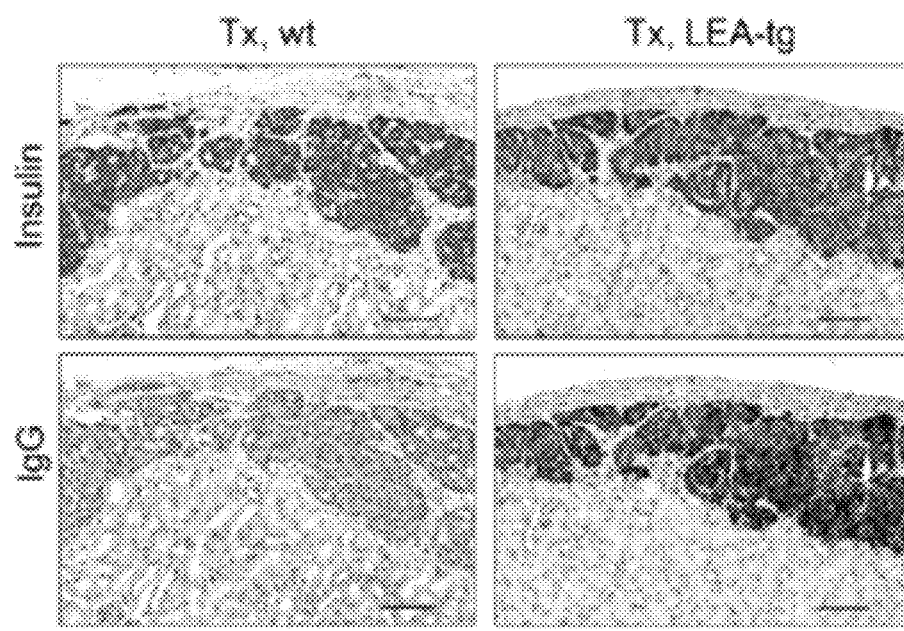

Mice transplanted with wild-type ICCs (Tx, wt; n=5) and mice transplanted with ICCs from LEA-tg pigs (Tx, LEA-tg; n=5) (insulin content 3.2±0.9 ng/µg protein) returned to normoglycemia after 51±7 and 43±7 days, respectively (FIG. 2A). Normoglycemic mice of both transplantation groups exhibited a comparable restored glucose tolerance (AUCglucose during i.p.GTT: Tx, wt: 12121±1303 Tx, LEA-tg: 11310±719) with similar glucose-responsive porcine insulin secretion (FIG. 2B). Immunohistochemical staining of the subcapsular graft revealed maturation of the transplanted ICCs towards a strongly insulin expressing endocrine tissue in both transplantation groups with LEA29Y transgene expression restricted to the grafts of Tx, LEA-tg mice (FIG. 2C, D). LEA29Y concentrations in the plasma of normoglycemic Tx, LEA-tg mice were 270±24 ng/ml.

INSLEA29Y Expression Prevents Re-Occurrence of Hyperglycemia

Figure 3A:
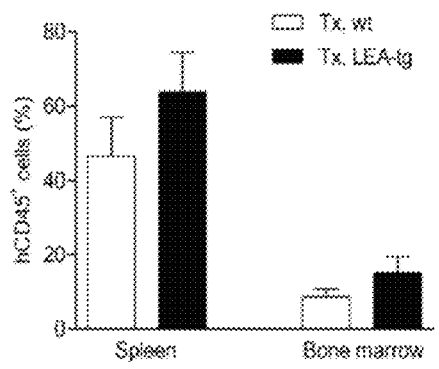
FIGS. 3A-3D—LEA29Y Expression Prevents Re-Occurrence of Hyperglycemia after Transfer of Human PBMCs.
(A) Engraftment of human PBMCs (as indicated by FACS staining for human $CD45^+$ cells in both spleen and bone marrow cells) did not significantly differ between mice transplanted with wild-type (Tx, wt) and in mice transplanted with LEA-tg (Tx, LEA-tg) ICCs. (B) 4 of 5 Tx, wt but no Tx, LEA-tg mice developed hyperglycemia within 29 days after human PBMC transfer. After removal of the graft-bearing kidney (uninephrectomy, Unx) of normoglycemic animals all mice returned to severe hyperglycemia indicating the absence of endogenous β-cell regeneration. Life-table analysis (C) revealed a significantly (p=0.016) higher proportion of hyperglycemia re-occurrence in Tx, wt as compared with Tx, LEA-tg mice. Furthermore, the AUC glucose and insulin during i.p.GTT was unchanged before and 27 days after the transfer of human PBMCs in Tx, LEA-tg mice (D). n=4-5 animals for each transplantation group. †, one animal died at day 26 due to graft-versus-host disease.
Figure 3B:
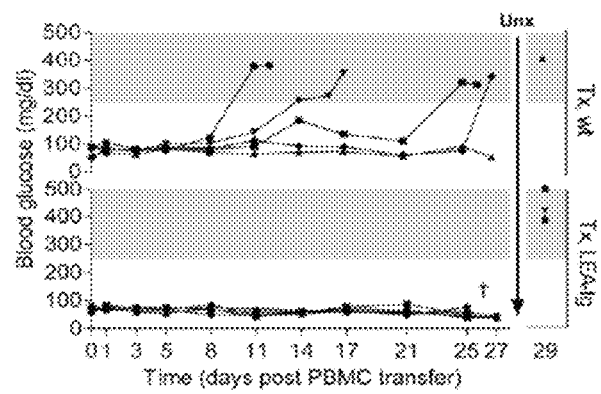
Figure 3C:
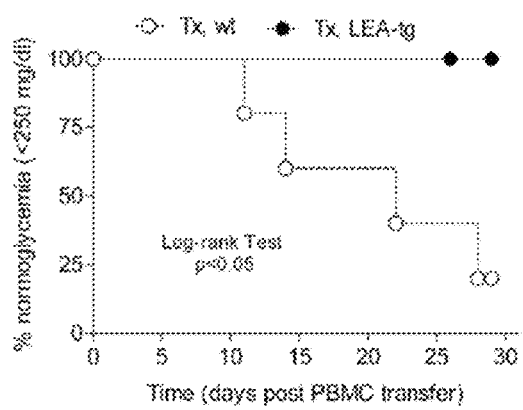
Figure 3D:
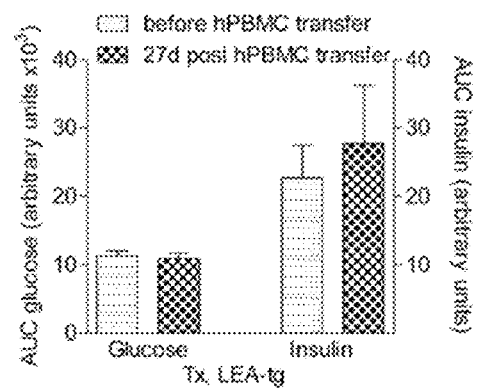
Figure 4:
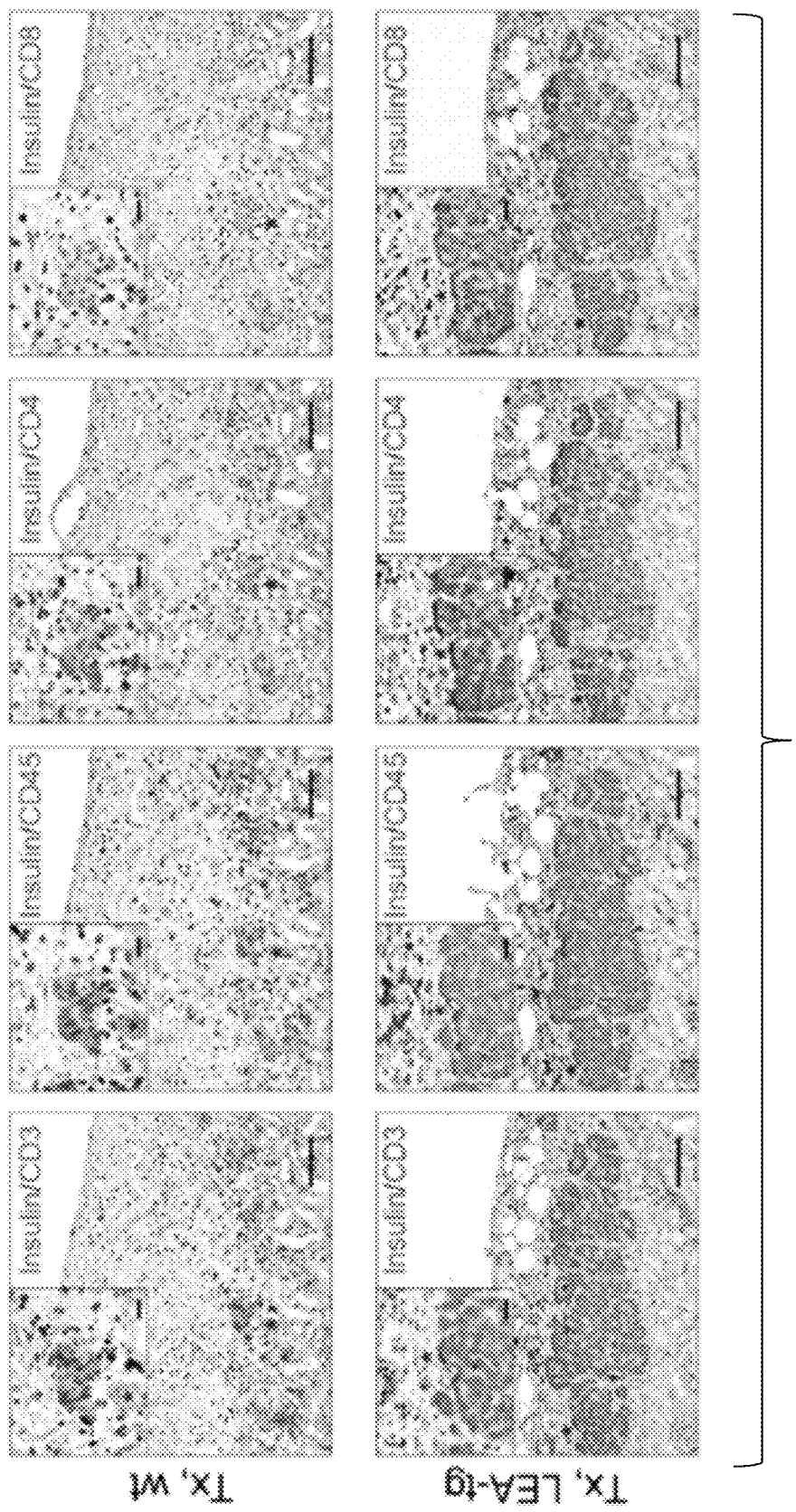
FIG. 4—LEA29Y Expressing ICCs are Almost Completely Preserved from Mononuclear Cell Infiltration.
Characteristic insulin (red) and $CD3^+$, $CD45^+$, $CD4^+$, and $CD8^+$ cell (brown) staining pattern of serial sections from the transplantation sites of a mouse transplanted with wild-type ICCs (Tx, wt; rejection at day 12 after PBMC transfer) vs. an animal with LEA29Y transgenic (Tx, LEA-tg, day 29 post PBMC transfer) (D). In Tx, wt only few ICCs were detectable with vast T cell ($CD3^+$, $CD4^+$, and $CD8^+$) and $CD45^+$ cell infiltration in the graft region. In contrast, Tx LEA-tg ICCs appeared completely preserved with T cell and leukocyte accumulation restricted to the subcapsular area (day 29 after Tx). The localization of tissue sections shown in the insets is marked by an asterisk. Scale bar: 100 µm, insets: scale bar 20 µm.
Figure 5:
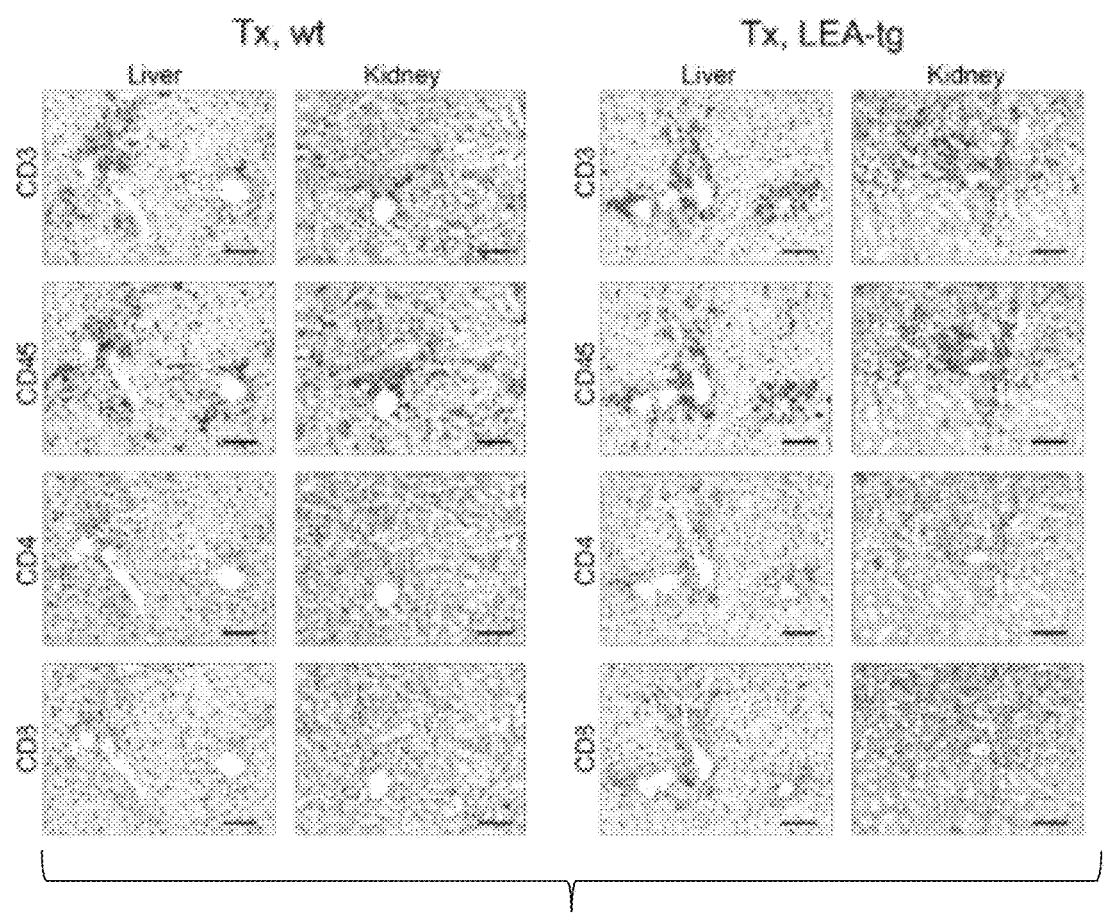
FIG. 5—Transplantation of LEA29Y Expressing ICCs Did not Influence the Development of Graft-Versus-Host Disease after Human PBMC Transfer.
Immunohistochemical staining of serial sections from the liver and the contralateral kidney revealed a comparable strong perivascular accumulation and tissue infiltration of $CD45^+$ leukocytes and $CD3^+$, $CD4^+$, and $CD8^+$ T lymphocytes in both mice transplanted with wild-type (Tx, wt) and LEA29Y transgenic ICCs (Tx, LEA-tg). Scale bar: 100 µm.

The finding that transgenic ICCs had strong LEA29Y expression and were able to normalize blood glucose levels raised the question whether these ICCs were protected from graft rejection after reconstitution with human PBMCs. The proportion of human CD45+ cells in the spleen and bone marrow was comparable in both transplantation groups (FIG. 3A) and histological examination revealed identical mononuclear cell infiltration in various tissues reflecting graft-versus host disease in both transplantation groups (FIG. 5). However, at day 14 after adoptive transfer of PBMCs blood glucose levels were significantly elevated in Tx, wt as compared to Tx, LEA-tg mice (204±63 mg/dl versus 58±2 mg/dl, p<0.05). Life table analysis revealed that re-occurrence of hyperglycemia, defined by blood glucose levels >250 mg/dl, was absent in Tx, LEA-tg mice (n=5) whereas four of five animals (80%) transplanted with wild-type ICCs became hyperglycemic within the observation period of 29 days (p<0.05) (FIG. 3B, C). One Tx, wt mouse remained normoglycemic throughout the observation period with preserved glucose tolerance at day 27. In three of the four hyperglycemic mice, porcine serum insulin was below the detection limit. In contrast, in all mice transplanted with LEA29Y transgenic ICCs the area under the glucose and insulin curve during i.p.GTT was comparable before and 27 d after transfer of human PBMCs (FIG. 3D). After removal of the graft bearing kidney, all of the diabetes-free animals returned to hyperglycemia (FIG. 3B). Histological examination of the graft bearing kidney from wild-type mice that developed hyperglycemia revealed a massive infiltration of ICCs with human mononuclear cells (CD3+, CD45+, CD4+, CD8+ cells) and reduced insulin staining. In contrast, in all Tx, LEA-tg mice ICCs appeared preserved and T cell infiltration was restricted to the surrounding tissue and almost absent within islet clusters (FIG. 4).

Discussion

Major obstacles in animal-to-human, such as pig-to-human, islet transplantation are the strong xenogeneic immune response and the severe adverse effects of the required intensive immunosuppressive regimen. To overcome these limitations we developed an islet donor animal that provides a local immunosuppressive environment within transplanted islets of Langerhans. The LEA-tg pigs generated in this study express high levels of LEA29Y specifically in the β-cells, with no signs of β-cell dysfunction or systemic immunosuppression such as increased susceptibility to opportunistic infections. This is in contrast to transgenic pigs with ubiquitous porcine CTLA-4Ig expression that were immune compromised and died of infections (Phelps et al., 2009). To assess the in vivo β-cell function and the immunomodulatory potential of LEA-tg islets, ICCs were transplanted into NSG mice, an established model for studying human immunity (Brehm et al., 2010, King et al., 2008). After an in vivo maturation period, which is required for immature ICCs to develop physiological insulin secretion (Korbutt et al., 1996), mice of both transplantation groups developed complete restoration of glucose homeostasis. These findings together with the strong, co-localized graft staining for insulin and LEA29Y indicate that LEA29Y expression in β-cells does not interfere with β-cell development and function. Previous transplantation studies in rats and non-human primates using high doses of Belatacept® for systemic immunosuppression, have also shown that co-stimulatory blockade by LEA29Y does not exert any adverse effects on β-cell function (Cardona et al., 2006, Tchorch-Yutsis et al., 2009).

After adoptive transfer of a human immune system, we observed that 80% of Tx, wt animals developed hyperglycemia whereas all Tx, LEA-tg mice were protected from graft rejection with preserved β-cell function. The development of hyperglycemia after xenograft removal indicated that glucose homeostasis was completely maintained by graft-derived porcine insulin secretion, excluding the possibility of endogenous β-cell regeneration. In Tx, LEA-tg mice human lymphocyte accumulation was observed in the periphery of the transplantation site and in the kidney, but LEA29Y-tg ICCs were protected from infiltration. Thus, our study shows for the first time that local expression of LEA29Y results in a prolonged islet xenograft function, supporting the hypothesis that inhibition of co-stimulation is able to modulate allo- and xenoimmunity (Hering et al., 2006, Cardona et al., 2007). These data are in line with findings from Zhai et al. demonstrating a prolonged survival of adenoviral vector transduced pig islets expressing porcine CTLA-4Ig (24). LEA29Y serum concentrations in recipients of LEA-tg ICCs were about 100-150 times lower as compared to systemic LEA29Y treatment in clinical trials (belatacept, BMS-224818), suggesting that graft protection is primarily mediated by local and not systemic LEA29Y immunomodulatory effects.

This is the first demonstration of prolonged islet xenograft function due to local immunosuppression from transgenic porcine islet tissue. Importantly, this work provides evidence for local protection of porcine tissue against human immune responses. In conclusion, this work serves as a proof-of-principle study demonstrating that local production of an immunomodulatory protein from transgenic porcine islet tissue can overcome the human-versus-porcine xenogeneic barrier. This study marks significant progress in bringing transgenic immunomodulation toward a clinical reality (see also Aikin 2012).

The following examples and drawings illustrate the present invention without, however, limiting the same thereto.

EXAMPLES

1. Materials and Methods

1.1 Animals

All experiments were approved by the local animal welfare authority. NSG mice were obtained from The Jackson Laboratory. For generation of INSLEA-tg pigs, the coding sequence for LEA29Y was cloned into a β-cell specific expression vector (1Grzech et al., 2010) with 1.3 kb upstream regions, exon 1 and intron 1 of the porcine insulin gene and a poly-adenylation cassette of the bovine growth hormone gene. The vector was completed by linking the INSLEA construct to a foxed neomycin resistance cassette (Aigner et al., 2010). Porcine fetal fibroblasts (PFF#14; $1\times10^6$) were nucleofected (Nucleofector™ technology, Lonza). Stably nucleofected cell clones were used as donors for somatic cell nuclear transfer (Kurome et al., 2006). Embryo transfer was carried out laparoscopically (Besenfelder et al., 1997). Integration and expression of the transgene was analyzed by Southern blot and immunohistochemistry. Donor piglets for transplantation experiments were generated by re-cloning as described previously (Aigner et al., 2010).

1.2 Isolation and Transplantation of Neonatal ICCs into Hyperglycemic NSG Mice Islet-cell-clusters (ICCs) from 1- to 2-day-old re-cloned LEA-tg and wild-type pigs were isolated as previously described (16) and cultured for 6 days at 37° C. in RPMI (Biochrom) with 2% human serum albumin (Octapharm), 1% antibiotic-antimycotic, 10 mM nicotinamide, and 20 nM exendine-4 (Sigma). Insulin content in ICCs was determined by ELISA (Millipore) (Pamir et al., 2003). 2500 clusters/mouse were transplanted under the kidney capsule of streptozotocin-diabetic (180 mg/kg, Sigma) NSG mice (blood glucose >350 mg/dl).

1.3 Characterization of Graft Function

Neonatal ICCs require a 6-8 week in vivo maturation period until physiological glucose-dependent insulin secretion has developed. Animals with blood glucose levels >300 mg/dl received exogenous insulin subcutaneously (0.5 IE glargine). Mice displaying blood glucose levels <150 mg/dl for a period of 5 days were considered normoglycemic. Intraperitoneal glucose tolerance testing (i.p.GTT) was performed 10 days later using 2 g glucose/kg body weight (Ayala et al., 2010). Porcine serum insulin was determined by ELISA (Mercodia) that displayed no cross-reactivity with mouse insulin. Serum LEA29Y concentrations were determined by sandwich ELISA using 1 µg/ml monoclonal anti-human-CTLA-4 antibody (Beckmann Coulter) and horseradish peroxidase (HRP)-conjugated polyclonal rabbit anti human IgG (DAKO).

1.4 Analyses in Humanized Mice

To analyze human-anti-pig immune response, $20\times10^6$ human PBMCs from one donor were transferred intraperitoneally into transplanted normoglycemic NSG mice as described previously (Hesselton et al., 1993). The remaining PBMCs were cultured in X-VIVO 20 medium (CambrexBio Science) supplemented with porcine splenocyte cell lysate (cytosolic fraction corresponding to $15\times10^6$ splenocytes) added at day 0 and day 3 to activate T cells directed against porcine antigens. After 6 days of culture, $2.5\times10^6$ primed hPBMCs were injected intravenously.

Reconstituted mice were monitored daily for re-occurrence of hyperglycemia. The investigation period was limited to 29 days due to the development of graft-versus-host disease. Animals displaying severe hyperglycemia (blood glucose levels >350 mg/dl in two consecutive measurements) were sacrificed ahead of schedule, whereas normoglycemic mice underwent i.p.GTT at day 27. To exclude endogenous β-cell regeneration, the graft of normoglycemic mice was removed at day 28 by uninephrectomy. From each animal blood and specimen for FACS analysis (FACS Canto, BD Biosciences) and immunohistochemistry (kidney, liver) were taken. Spleen and bone marrow cells were stained using the following fluorochrome-labeled monoclonal antibodies: mouse CD45-FITC, human CD45-APC or matched isotype antibodies (eBioscience).

1.5 Immunohistochemical Analyses

Pig organs and graft bearing kidneys were processed as described previously (Renner et al., 2010). Serial paraffin sections were stained with guinea pig anti-insulin (1:500), rabbit anti-human CD3 (1:100), rabbit anti-human IgG (recognizing the C-terminal part of LEA29Y; 1:50), mouse anti-human CD4 (1:20) (DAKO), rabbit anti-human CD8 (1:80; Vector), and rabbit anti-human CD45 (1:400; antibodies-online). As secondary antibodies HRP-conjugated anti-guinea pig IgG, anti-rabbit IgG, biotinylated anti-rabbit IgG or anti-mouse IgG (DAKO), and alkaline phosphatase-conjugated anti-guinea pig IgG (Southern Biotech) were used. Chromogens included Fuchsin+Substrate Chromogen (DAKO) or DAB (Kem-En-Tee Diagnostics) (Renner et al., 2010).

1.6 Data Presentation and Statistical Analysis

Data represent means and SEM. Statistical analyses were performed using the Student's t-test or log-rank test (diabetes re-occurrence). P values <0.05 were considered significant.

The features disclosed in the foregoing description, in the claims and/or in the accompanying drawings may, both separately and in any combination thereof, be material for realizing the invention in diverse forms thereof.

REFERENCES

Aigner B, Renner S, Kessler B, Klymiuk N, Kurome M, Wunsch A, Wolf E: Transgenic pigs as models for translational biomedical research. *J Mol Med (Berl)* 88:653-664, 2010.

Aikin R A: How to kill two birds with one transgenic pig. *Diabetes.* 2012 June; 61(6):1348-9.

Ayala J E, Samuel V T, Morton G J, Obici S, Croniger C M, Shulman G I, Wasserman D H, McGuinness O P: Standard operating procedures for describing and performing metabolic tests of glucose homeostasis in mice. *Dis Model Mech* 3:525-534, 2010.

Besenfelder U, Modl J, Muller M, Brem G: Endoscopic embryo collection and embryo transfer into the oviduct and the uterus of pigs. *Theriogenology* 47:1051-1060, 1997.

Bottino R, Trucco M. Multifaceted therapeutic approaches for a multigenic disease. *Diabetes.* 2005 December; 54 Suppl 2:S79-86. Review.

Brehm M A, Shultz L D, Greiner D L: Humanized mouse models to study human diseases. *Curr Opin Endocrinol Diabetes Obes* 17:120-125, 2010.

Cardona K, Korbutt G S, Milas Z, Lyon J, Cano J, Jiang W, Bello-Labom H, Hacquoil B, Strobert E, Gangappa S, Weber C J, Pearson T C, Rajotte R V, Larsen C P: Long-term survival of neonatal porcine islets in nonhuman primates by targeting costimulation pathways. *Nat Med* 12:304-306, 2006.

Cardona K, Milas Z, Strobert E, Cano J, Jiang W, Safley S A, Gangappa S, Hering B J, Weber C J, Pearson T C, Larsen C P: Engraftment of adult porcine islet xenografts in diabetic nonhuman primates through targeting of costimulation pathways. *Am J Transplant* 7:2260-2268, 2007.

CITR: 2007 update on allogeneic islet transplantation from the Collaborative Islet Transplant Registry (CITR). *Cell Transplant* 18:753-767, 2009.

Clarkson M R, Sayegh M H: T-cell costimulatory pathways in allograft rejection and tolerance. *Transplantation* 80:555-563, 2005

Durrbach A, Pestana J M, Pearson T, Vincenti F, Garcia V D, Campistol J, Rial Mdel C, Florman S, Block A, Di Russo G, Xing J, Garg P, Grinyo J: A phase III study of belatacept versus cyclosporine in kidney transplants from extended criteria donors (BENEFIT-EXT study). *Am J Transplant* 10:547-557, 2010.

Elliot R B, Escobar L, Tan P L, Garkavenko O, Calafiore R, Basta P, Vasconcellos A V, Emerich D F, Thanos C, Bambra C. Intraperitoneal alginate-encapsulated neonatal porcine islets in a placebo-controlled study with 16 diabetic cynomolgus primates. *Transplant Proc.* 37(8):3505-8, 2005.

Elliot R B, Escobar L, Tan P L, Muzina M, Zwain S, Buchanan C. Live encapsulated porcine islets from a type 1 diabetic patient 9.5 yr after xenotransplantation. *Xenotransplantation.* 14(2):157-61, 2007.

Grzech M, Dahlhoff M, Herbach N, Habermann F A, Renner-Muller I, Wanke R, Flaswinkel H, Wolf E, Schneider M R: Specific transgene expression in mouse pancreatic beta-cells under the control of the porcine insulin promoter. *Mol Cell Endocrinol* 315:219-224, 2010.

Hecht G, Eventov-Friedman S, Rosen C, Shezen E, Tchorsh D, Aronovich A, Freud E, Golan H, El-Hasid R, Katchman H, Hering B J, Zung A, Kra-Oz Z, Shaked-Mishan P, Yusim A, Shtabsky A, Idelevitch P, Tobar A, Harmelin A, Bachar-Lustig E, Reisner Y. Embryonic pig pancreatic tissue for the treatment of diabetes in a nonhuman primate model. *Proc Natl Acad Sci USA.* 106(21):8659-64, 2009.

Hering B J, Wijkstrom M, Graham M L, Hardstedt M, Aasheim T C, Jie T, Ansite J D, Nakano M, Cheng J, Li W, Moran K, Christians U, Finnegan C, Mills C D, Sutherland D E, Bansal-Pakala P, Murtaugh M P, Kirchhof N, Schuurman H J: Prolonged diabetes reversal after intraportal xenotransplantation of wild-type porcine islets in immunosuppressed nonhuman primates. *Nat Med* 12:301-303, 2006.

Hesselton R M, Koup R A, Cromwell M A, Graham B S, Johns M, Sullivan J L: Human peripheral blood xenografts in the SCID mouse: characterization of immunologic reconstitution. *J Infect Dis* 168:630-640, 1993.

King M, Pearson T, Rossini A A, Shultz L D, Greiner D L: Humanized mice for the study of type 1 diabetes and beta cell function. *Ann N Y Acad Sci* 1150:46-53, 2008, Korbutt G S, Elliott J F, Ao Z, Smith D K, Warnock G L, Rajotte R V: Large scale isolation, growth, and function of porcine neonatal islet cells. *J Clin Invest* 97:2119-2129, 1996.

Kurome M, Ueda H, Tomii R, Naruse K, Nagashima H: Production of transgenic-clone pigs by the combination of ICSI-mediated gene transfer with somatic cell nuclear transfer. *Transgenic Res* 15:229-240, 2006.

Larsen C P, Pearson T C, Adams A B, Tso P, Shirasugi N, Strobert E, Anderson D, Cowan S, Price K, Naemura J, Emswiler J, Greene J, Turk L A, Bajorath J, Townsend R, Hagerty D, Linsley P S, Peach R J: Rational development of LEA29Y (belatacept), a high-affinity variant of CTLA4-Ig with potent immunosuppressive properties. *Am J Transplant* 5:443-453, 2005.

London N J, Swift S M, Clayton H A: Isolation, culture and functional evaluation of islets of Langerhans. *Diabetes Metab.* 1998 June; 24(3):200-7. Review.

Nathan D M, Zinman B, Cleary P A, Backlund J Y, Genuth S, Miller R, Orchard T J: Modern-day clinical course of type 1 diabetes mellitus after 30 years' duration: the diabetes control and complications trial/epidemiology of diabetes interventions and complications and Pittsburgh epidemiology of diabetes complications experience (1983-2005). *Arch Intern Med* 169:1307-1316, 2009.

Pamir N, Lynn F C, Buchan A M J, Ehses J, Hinke S A, Pospisilik J A, Miyawaki K, Yamada Y, Seino Y, McIntosh C H S, Pederson R A: Glucose-dependent insulinotropic polypeptide receptor null mice exhibit compensatory changes in the enteroinsular axis. *American Journal of Physiology-Endocrinology and Metabolism* 284:E931-E939, 2003.

Phelps C J, Ball S F, Vaught T D, Vance A M, Mendicino M, Monahan J A, Walters A H, Wells K D, Dandro A S, Ramsoondar J J, Cooper D K, Ayares D L. Production and characterization of transgenic pigs expressing porcine CTLA4-Ig. *Xenotransplantation.* 16(6):477-85, 2009.

Renner S, Fehlings C, Herbach N, Hofmann A, von Waldthausen D C, Kessler B, Ulrichs K, Chodnevskaja I, Moskalenko V, Amselgruber W, Goke B, Pfeifer A, Wanke R, Wolf E: Glucose intolerance and reduced proliferation of pancreatic beta-cells in transgenic pigs with impaired glucose-dependent insulinotropic polypeptide function. *Diabetes* 59:1228-1238, 2010.

Robertson R P: Islet transplantation a decade later and strategies for filling a half-full glass. *Diabetes* 59:1285-1291, 2010.

Schuurman H J. The International Xenotransplantation Association consensus statement on conditions for undertaking clinical trials of porcine islet products in type 1 diabetes—chapter 2: Source pigs. *Xenotransplantation.* 2009 July-August; 16(4):215-22.

Tchorsh-Yutsis D, Hecht G, Aronovich A, Shezen E, Klionsky Y, Rosen C, Bitcover R, Eventov-Friedman S, Katchman H, Cohen S, Tal O, Milstein O, Yagita H, Blazar B R, Reisner Y: Pig embryonic pancreatic tissue as a source for transplantation in diabetes: transient treatment with anti-LFA1, anti-CD48, and FTY720 enables long-term graft maintenance in mice with only mild ongoing immunosuppression. *Diabetes* 58:1585-1594, 2009.

Toso C, Brandhorst D, Oberholzer J, Triponez F, Baler L, Morel P. Isolation of adult porcine islets of Langerhans. *Cell Transplant.* 2000 May-June; 9(3):297-305.

Ulrichs K., Eber S., Schneiker B, Gahn S, Strauβ A, Moskalenko V, Chodnevskaja I: Isolation of porcine pancreatic islets for xenotransplantation. *Methods Mol. Biol.* 2012; 885:213-32.

Vincenti F, Charpentier B, Vanrenterghem Y, Rostaing L, Bresnahan B, Darji P, Massari P, Mondragon-Ramirez G A, Agarwal M, Di Russo G, Lin C S, Garg P, Larsen C P: A phase III study of belatacept-based immunosuppression regimens versus cyclosporine in renal transplant recipients (BENEFIT study). *Am J Transplant* 10:535-546, 2010.

Zhai C, Yu L, Zhu H, Tian M, Xiaogang Z, Bo W: Porcine CTLA4-Ig prolong islet xenografts in rats by downregulating the direct pathway of T-cell activation. *Xenotransplantation* 18:40-45, 2011.

We claim:

1. A method of treating diabetes in a human subject, comprising the steps of:
   1) isolating pancreatic islets of a transgenic animal, wherein said transgenic animal is a transgenic animal whose genome comprises a recombinant nucleic acid consisting essentially of a polynucleotide sequence encoding a CTLA4 peptide fused to an immunoglobulin ("CTLA4 peptide-immunoglobulin fusion"), wherein said polynucleotide sequence is operably linked to an insulin promoter that results in expression of the CTLA4 peptide-immunoglobulin fusion in said animal, wherein said expression is stable in offspring of said transgenic animal, and wherein said animal exhibits, as a result of the expression of said CTLA4 peptide-immunoglobulin fusion, tissue-specific expression of the CTLA4 peptide-immunoglobulin fusion in pancreatic islets; and
   2) administering said isolated pancreatic islets of the transgenic animal into a human subject in need thereof, wherein said isolated pancreatic islets of the transgenic animal have the ability to normalize blood glucose levels in the human subject into which the islets are administered, wherein after xenotransplantation of said transgenic pancreatic islets of said animal into a human subject, said transgenic pancreatic islets are protected from rejection by mature human immune system cells, and prevent re-occurrence of hyperglycemia.

2. The method of claim 1, wherein the transgenic animal does not exhibit an immunodeficient phenotype.

3. The method of claim 1, wherein the recombinant nucleic acid is an expression construct, a plasmid or viral vector.

4. The method of claim 3, wherein the insulin promoter is pig INS promoter, rat insulin 2 gene promoter (RIPII), or PDX1 promoter.

5. The method of claim 1, wherein the recombinant nucleic acid encodes the CTLA4 peptide-immunoglobulin fusion that is LEA29Y.

6. The method of claim 1, wherein the recombinant nucleic acid encodes a protein comprising the sequence of SEQ ID NO. 1.

7. The method of claim 1, wherein the transgenic animal contains the recombinant nucleic acid in its germ cells and somatic cells.

8. The method of claim 1, wherein LEA29Y is expressed in the pancreatic islets.

9. The method of claim 1, wherein the transgenic pancreatic islets of said animal display the same potential to normalize glucose homeostasis as wild type cells.

10. The method of claim 1, wherein the human subject requires less administration of immunosuppressive agents compared to standard therapy and/or compared to xenotransplantation of wild type pancreatic islets of an animal.

11. The method of claim 1, wherein the transgenic animal is a pig, bovine, or small ruminant.

12. The method of claim 1, wherein the diabetes treated is diabetes type 1 and/or diabetes type 2.

13. The method of claim 1, wherein the transgenic pancreatic islets are encapsulated or micro-encapsulated before administration.

14. The method of claim 13, wherein the encapsulated or micro-encapsulated transgenic pancreatic islets are administered by implantation.

15. The method of claim 1, wherein said transgenic islets are transplanted into the omentum or under the kidney capsule of the human subject and the human subject requires less administration of immunosuppressive agents compared to standard therapy and/or compared to xenotransplantation of wild type pancreatic islets of an animal.

16. The method, according to claim 1, wherein said transgenic animal is a pig.

* * * * *

UNITED STATES PATENT AND TRADEMARK OFFICE
CERTIFICATE OF CORRECTION

PATENT NO. : 10,286,013 B2
APPLICATION NO. : 15/336350
DATED : May 14, 2019
INVENTOR(S) : Eckhard Wolf et al.

Page 1 of 1

It is certified that error appears in the above-identified patent and that said Letters Patent is hereby corrected as shown below:

In the Specification

<u>Column 2,</u>
Lines 62-67, "expression of the CTLA4 peptide-immunoglobulin fusion, wherein said animal expresses the CTLA4 peptide-immunoglobulin fusion, and wherein said animal exhibits, as a result of the CTLA4 peptide-immunoglobulin fusion in the transgenic embryonic pancreas or transgenic embryonic pancreatic tissue." should read --expression of the CTLA4 peptide-immunoglobulin fusion, wherein said animal expresses the CTLA4 peptide-immunoglobulin fusion, and wherein said animal exhibits, as a result of the expression of said CTLA4 peptide-immunoglobulin fusion, tissue-specific expression of the CTLA4 peptide-immunoglobulin fusion in the transgenic embryonic pancreas or transgenic embryonic pancreatic tissue.--.

<u>Column 12,</u>
Line 50, "(Kem-En-Tee Diagnostics)" should read --(Kem-En-Tec Diagnostics)--.

<u>Column 15,</u>
Line 5, "Baler" should read --Bühler--.

Signed and Sealed this
First Day of October, 2019

Andrei Iancu
*Director of the United States Patent and Trademark Office*